(12) United States Patent
Fan et al.

(10) Patent No.: US 7,357,935 B2
(45) Date of Patent: Apr. 15, 2008

(54) **AVIAN *E. COLI* VACCINE FOR PROTECTION AGAINST COLIBACILLOSIS**

(75) Inventors: Henry H. Fan, Hickory, NC (US); Mahesh Kumar, Fort Dodge, IA (US); Roberto Marcello La Ragione, Potters Bar (GB); Martin John Woodward, Farnborough (GB)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/837,793

(22) Filed: May 3, 2004

(65) Prior Publication Data

US 2004/0234534 A1 Nov. 25, 2004

Related U.S. Application Data

(60) Provisional application No. 60/470,471, filed on May 14, 2003.

(51) Int. Cl.
*A61K 39/108* (2006.01)
(52) U.S. Cl. .................. 424/257.1; 424/234; 435/243; 435/252.3
(58) Field of Classification Search ............. 424/234.1, 424/257.1; 435/243, 252.3
See application file for complete search history.

(56) References Cited

U.S. PATENT DOCUMENTS

| 4,837,018 | A | 6/1989 | Konishi et al. |
| 5,641,491 | A | 6/1997 | Wilson et al. |
| 6,231,871 | B1 | 5/2001 | Coloe |
| 6,350,454 | B1 * | 2/2002 | Thune ..................... 424/200.1 |
| 6,902,906 | B1 | 6/2005 | Chatfield |
| 2004/0234550 | A1 | 11/2004 | Fan |

FOREIGN PATENT DOCUMENTS

| EP | 0400958 A2 | 12/1990 |
| EP | 0650733 A1 | 5/1995 |

OTHER PUBLICATIONS

Molina et al. (Infect.Immun. 58(8): 2523-2528. Aug. 1990).*
Maskell et al (Microbial Pathogenesis. 293: 211-221. Mar. 1987. ABSTRACT only).*
Stocker (J.Biotech. 83: 45-50. 2000).*
Edwards et al. (J.Bacteriol. Sep. 1998. 170(9): 3991-3995).*
Bowie et al., "Deciphering the Message in Protein Sequences: Tolerance to Amino Acid Substitutions," Science, col. 247, pp. 1306-1310 (1990).*
Gerald L. Cooper, et al, "Vaccination of chickens with a *Salmonella enteritidis* aroA live oral *salmonella* vaccine" Microbial Pathogenesis 1990; 9: 255-265.
Erik P. Lillehoj, et al, "Vaccines against the avian enteropathogens Eimeria, Cryptosporidum and *Salmonella*" Animal Health Research Reviews 1(1); 47-65.
Nature, 1974, vol. 252, pp. 252-254.
George F. Dancey, et al., "Effect of Liposomal Model Membrane Composition on Immunogenicity," The Journal of Immunology, Apr. 1978, vol. 120, No. 4, pp. 1109-1113.
R.M. La Ragione, et al., "The role of fimbriae and flagella in the colonization, invasion and persistence of *Escherichia coli* O78:K80 in the day-old-chick model," Epidemiology and Infection, 2000, vol. 124, pp. 351-363.
R.M. La Ragione, et al., "The role of fimbriae and flagella in the adherence of avian strains of *Escherichia coli* O78:K80 to tissue culture cells and tracheal and gut explants," Journal of Medical Microbiology, 2000, vol. 49, pp. 327-338.
S. N. Chatfield et al.; Vaccine; vol. 10; Issue 1; pp. 53-60; 1992.
Wang; Fowl. Sci. Tech. 14:24, 1998 (in Chinese, cited in Office Action from Chinese Patent Office. A copy of the Office Action is included in accordance with MPEP § 609.04(a)(III)).
Hassan et al.; Res. Microbiol. 141:839-850, 1990.
Wang et al.; Microb. Pathog. 27:55-59, 1999.
Peighambari et al.; Avian Dis. 46:287-297, 2002.

* cited by examiner

*Primary Examiner*—Jennifer E. Graser
(74) *Attorney, Agent, or Firm*—Maria Restreo-Hartwig

(57) ABSTRACT

A genetic deletion mutant live *E. coli* vaccine suitable for mass application to poultry, including chickens, is provided. Also provided is a safe and effective method to protect poultry against the ravages of *Escherichia coli* bacillosis infection and disease in which a live mutant aroA-gene deleted *E. coli* immunogen is administered to chickens, turkeys and the like via mass application routes such as coarse sprays and drinking water.

17 Claims, No Drawings

AVIAN *E. COLI* VACCINE FOR PROTECTION AGAINST COLIBACILLOSIS

This application claims priority from provisional Application Ser. No. 60/470,471 now abandoned, filed May 14, 2003, the entire disclosure of which is hereby incorporated herein by reference.

FIELD OF THE INVENTION

The present invention relates to avian vaccines against *E. coli* infection. In particular, the invention is directed to mutant strain *E. coli* vaccines which are useful for poultry, and especially chickens. The invention also relates to a novel aroA gene-deleted *E. coli* microorganism immunogen which is useful and effective in a vaccine via spray or drinking water against *E. coli*-induced colibacillosis, a devastating poultry illness.

BACKGROUND OF THE INVENTION

Colibacillosis is a common systemic disease of economic importance in poultry and occurs worldwide. This *Escherichia coli* (*E. coli*) infection occurs as an acute fatal septicemia or subacute pericarditis and airsacculitis, as well as perihepatitis, arthritis, and also cellulitis. Among bacterial infections, colibacillosis is very often the first cause of morbidity and mortality in poultry. Large numbers of *E. coli* are maintained in the poultry house environment through fecal contamination. Systemic infection occurs when large numbers of pathogenic *E. coli* gain access to the bloodstream via the respiratory tract or intestine. Bacteremia progresses to septicemia and death, or the infection extends to serosal surfaces, pericardium, joints and other organs.

The literature suggests that serotypes O1, O2 and O78 of *E. coli* associated with colibacillosis are the most common serotypes found in chickens and turkeys. Many isolated strains are also untypeable and are considered especially virulent.

Treatment strategies include control of predisposing infections or environmental factors, and early use of antibiotics. Unfortunately, a high frequency of resistance to tetracycline, kanamycin, neomycin, cephalotin, streptomycin and erythromycin has been observed. Many strains are also resistant to several antibiotics. Wide spread sensitivity to ampicillin and chloramphenicol has also been observed.

Although there is a commercial live *E. coli* vaccine available for use against colibacillosis associated with infection by *E. coli* O78 in turkeys, there appears to be no fully safe and effective *E. coli* vaccines for use in chickens. In particular, there does not appear to be any live, attenuated, mutant aroA gene-deleted *E. coli* vaccine for poultry commercially available. There also does not appear to be an especially efficacious *E. coli* vaccine that is suitable for mass administration via aerosol spray or drinking water, for example.

Therefore, it is an object of this invention to provide a safe and effective live *E. coli* vaccine, suitable for use in chickens.

It is another object of this invention to provide a method for the prevention or amelioration of colibacillosis in poultry which is safe and effective when used in chickens.

It is a feature of this invention that the *E. coli* vaccine is suitable for mass application.

It is an advantage of this invention that the live vaccine provides both a good cellular and a good humoral immunity response in the host.

SUMMARY OF THE INVENTION

The present invention provides the gene deleted *Escherichia coli* mutant, *E. coli* aroA-microorganism having the identifying characteristics of the strain which was deposited with the American Type Culture Collection and assigned number PTA-5094.

The present invention also provides an avian vaccine composition which comprises an immunogenically effective amount of said *E. coli* aroA-microorganism and a pharmacologically acceptable carrier.

The present invention further provides a method for the prevention or amelioration of colibacillosis in poultry which comprises administering to said poultry an immunogenically effective amount of said *E. coli* aroA-microorganism.

Further provided as part of the invention is a vaccine for chickens and other poultry against colibacillosis which comprises an immunogenically effective amount of an *E. coli* aroA-deletion mutant in a pharmacologically acceptable carrier.

Other features of the invention will be come more apparent from the detailed description set forth hereinbelow.

DETAILED DESCRIPTION OF THE INVENTION

Avian colibacillosis in domestic poultry is frequently associated with *Escherichia coli* (*E. coli*) serotype O78. Infection commonly occurs via the respiratory tract, often following exposure to, or infection by, other poultry community diseases such as mycoplasmosis, infectious bronchitis, Newcastle's disease, hemorrhagic enteritis or turkey bordetellosis. In chickens, colibacillosis generally affects broilers between 3 to 10 weeks of age and is associated with high morbidity and mortality. The most severe manifestation of avian colibacillosis is septicemia which is characterized by pericarditis, perihepatitis and airsacculitis. Cellulitis is also a formidable problem. Isolates of *E. coli* from poultry are frequently resistant to drugs such as ampicillin, chloramphenicol, oxytetracycline, neomycin, gentamicin, nitrofurans, nalidixic acid, polymixin B, sulfonamides, or the like. Moreover, at present, there appears to be no commercially available *E. coli* vaccines for chickens.

Surprisingly, it has now been found that the *E. coli* aroA deletion mutant, *E. coli* aroA—deposited with the American Type Culture Collection (ATCC) at 10801 University Boulevard, Manassas, Va. 20110 USA on Mar. 27, 2003 and having ATCC accession number PTA-5094 is safe and effective for use against avian colibacillosis in chickens. Advantageously, the *E. coli* aroA-PTA-5094 of the invention, when administered to chickens, provides good cellular and humoral immune responses and said *E. coli* aroA-PTA-5094 may be easily produced and may be administered via mass application, e.g. coarse spray or drinking water.

As used in the specification and claims, the term *E. coli* aroA-PTA-5094 designates the *Escherichia coli* aroA deletion mutant microorganism which was deposited with the ATCC on Mar. 27, 2003 and was assigned ATCC number PTA-5094. This term is also intended to encompass other strains of *E. coli* aroA-gene-deletion mutants which are prepared in substantially the same manner as set forth herein, and which have substantially the same immunogenic characteristics thereof.

The *E. coli* aroA gene deleted mutant strain of the invention may be further serially passaged using media and techniques available to the skilled artisan. Serial passaging can serve to further attenuate the strain to make it more suitable as a vaccine immunogen. Up to about 10 serial passages are contemplated herein, with about 3 to 5 being preferred.

The *E. coli* aroA deletion mutant of the invention has the distinct advantage that the surface appendages such as type 1 fimbriae and flagella, which have been shown to be important in the pathogenesis of avian colibacillosis, are still expressed. (LaRagione, R. M.; Sayus, A. R.; and Woodward, M. J., *Epidemiology and Infection*, 2000,124:351-363 and LaRagione, R. M.; Cooly, W. A.; and Woodward, M. J., *Journal of Medical Microbiology*, 2000, 49:327-338). Fully defined genetic deletion vaccines are preferable as candidates for live vaccines, offering the potential of combined safety and a high degree of efficacy in the host. Particularly desirable are deletion mutants that cannot revert to a wild-type phenotype. In actual practice, a defined *E. coli* aroA-mutant deficient for the biosynthesis of aromatic amino acids was constructed in a pathogenic *E. coli* strain to produce the *E. coli* aroA-PTA-5094 of the invention. Said *E. coli* aroA-PTA-5094 is safe and efficacious in chicks against a wild-type *E. coli* challenge. Accordingly, the present invention also provides a method for the prevention or amelioration of avian colibacillosis in poultry which comprises administering to said poultry an immunogenically effective amount of *E. coli* aroA-PTA-5094.

Immunogenically effective amounts may vary according to the age and size of the host, the severity of the infection, the virility of the pathogen, the mode of administration or the like. In general, suitable effective amounts per dosage unit may be about $10^2$ to $10^{14}$ colony forming units (cfu), preferably about $5.0 \times 10^2$ to $5.0 \times 10^{10}$ cfu, more preferably about $3.0 \times 10^6$ cfu to $6.0 \times 10^6$ cfu, and even more preferably about $5.0 \times 10^6$ cfu to $6.0 \times 10^6$ cfu. One or two dosage units may be contemplated by the skilled artisan. If two dosage units are selected, then vaccination at about day 1 post-hatch and again at about one week to two weeks of age is preferred. A dosage unit is desirably about 0.5 to 1 mL of vaccine per bird, but that quantity may be optimized to deliver an immunogenically effective amount of the microorganism immunogen hereinabove described.

Poultry suitable for use in the method of invention include chickens, ducks, turkeys, geese, bantams, quail, pheasant, pigeons, or the like, preferably commercially important poultry such as chickens, ducks, geese and turkeys, more preferably chickens and turkeys, particularly preferably chickens.

The *E. coli* aroA-PTA-5094 of the invention may be administered by any conventional means, preferably an economically viable means for the poultry industry such as mass administration via spray or drinking water. It is quite unexpected that *E. coli*, a natural pathogen of the respiratory mucosa, can be applied via a spray (preferably aerosol) route, and still be safe as well as efficacious. It would normally be expected that a vaccine against such a potently lethal pathogen, especially bacteria, should only be provided via injection or some other route. The aroA-mutation strain of the invention is safe for spray administration. In actual practice, the *E. coli* aroA-PTA-5094 is admixed with a liquid carrier and administered as a spray or as a drinking water additive. Accordingly, the present invention further provides an avian vaccine composition which comprises an immunogenically effective amount of *E. coli* aroA-PTA-5094 and a pharmacologically acceptable carrier.

Pharmacologically acceptable carriers suitable for use in the vaccine composition of the invention may be any conventional liquid carrier suitable for veterinary pharmaceutical compositions, preferably a balanced salt solution suitable for tissue or cell culture media such as sterile phosphate buffered saline, more preferably distilled water. Other suitable media can include emulsions. The vaccine of the invention may also be adjuvanted by the skilled technician. When application of the vaccine is via drinking water, non-fat dry milk may be utilized as a carrier. The non-fat dry milk appears to stabilize the vaccine, and perhaps neutralizes the action of some trace minerals that can affect viability.

In addition to the *E. coli* aroA-PTA-5094 microorganism as active ingredient, it is contemplated the vaccine composition of the invention may also contain other active components such as an avian immunogenic antipathogenic compound directed against avian leukosis, reticuloendotheliosis, infectious bronchitis, infectious bursal disease, Newcastle disease, avian adenovirus disease, avian reovirus disease, fowl pox disease, infectious laryngotracheitis, avian influenza, infectious coryza, fowl typhoid, coccidiosis, cryptosporidiosis, fowl cholera, or the like.

In one embodiment of the invention, the *E. coli* aroA-PTA-5094 microorganism of the invention may be incorporated into liposomes using known technology such as that described in *Nature*, 1974, 252:252-254 or *Journal of Immunology*, 1978, 120:1109-1113. In another embodiment of the invention, the *E. coli* aroA-PTA-5094 microorganism of the invention may be conjugated to suitable biological compounds such as polysaccharides, peptides, proteins, or the like, or a combination thereof using protocol available to the skilled artisan.

The vaccine of the invention according to the embodiments herein described is to be considered efficacious against all serotypes of *E. coli* colibacillosis, including serotypes O1, O2 and O78, as well as the especially virulent untyped serotypes. The vaccine herein described is efficacious against septicemia, pericarditis, airsacculitis, periphepatitis, arthritis, and particularly cellulitis. The latter is often associated with colibacillosis, but can be a significant problem in itself.

For a more clear understanding of the invention, the following examples are set forth below. These examples are merely illustrative and are not understood to limit the scope or underlying principles of the invention in any way. Indeed, various modifications of the invention, in addition to those shown and described herein, will become apparent to those skilled in the art from the examples set forth hereinbelow and the foregoing description. Such modifications are also intended to fall within the scope of the appended claims.

EXAMPLE 1

Construction of aroA Gene Deleted *E. coli* Mutant

I) Recipient

The parental organism is an avian isolate of *E. coli* isolated from a clinical case of avian colibacillosis submitted to the Veterinary Laboratories Agency (VLA), Addlestone, Surrey, UK and serotyped at VLA in 1995. The parent strain was selected for its colonization, invasion, persistence and pathogenicity in one-day-old SPF chicks and by in vitro characterization for its antibiotic sensitivity pattern. The recipient strain was generated by conjugation between the transformed donor (*E. coli* K12 S17 λ pir harboring PNG101 with aroA harboring 100 bp deletion) and wild-type parent strain (wild-type *E. coli* isolate EC34195).

II) Characterization of the Deletion

The aroA gene, which encodes 3-phosphoenolpyruvylshikimate-5-phosphate synthetase, an enzyme of the common aromatic biosynthetic pathway, is located adjacent and promoterdistal to serC in the serC-aroA operon. Loss of function for the aroA gene in the recipient results in a requirement for aromatic metabolites, including tyrosine, phenylalanine, tryptophan, p-aminobenzoate (PABA) and 2,3-dihydroxybenzoate. The requirement for PABA, a metabolite not found in vertebrate tissues, results in attenuation of in vivo growth.

III) Construction of the aroA Deleted *E. coli* Mutant a) PCR primers are designed incorporating SrtI and BglII restriction sites and stop codons to amplify two separate PCR products of approximately 650 bp for the 5' and 3' ends of the aroA gene from the poultry *E. coli* O78 isolate described above.

b) Both PCR products are digested with BglII for 2 hours, electrophoresis is run for 1 hour at 100 volts, the bands are excised and the respective bands are purified using SephaGlas bandprep kit.

c) Equal volumes of each purified PCR product are mixed and ligated into pCR2. 1.

d) Ligated plasmid harboring aroA are transformed into DH5α maxi-competent cells and cloning is confirmed by restriction enzyme mapping and PCR.

e) Complete aroA gene with deletion from pCR2.1 is excised with EcorV and SpeI then purified and ligated into a predigested (SpeI) suicide vector (SacB, pKNG101), transformed into competent *E. coli* K12 S17 λ pir and cloning is confirmed by restriction enzyme mapping and PCR.

f) A conjugation is performed between donor (*E. coli* S17 λ pir harboring pKNG101 with aroA harboring 100 bp deletion) and wild-type *E. coli* isolate.

g) Colonies appearing after 48 hours incubation at 37° C. are subcultured onto minimal media supplemented with gentamicin and streptomycin and aromatic amino acids (20 mg/l of each of DL tryptophan, DL phenylalanine and DL tyrosine). Individual colonies are tested by PCR. Colonies that yielded a wild-type PCR product and mutated PCR product of some 100 bp smaller are retained for further studies.

h) Single crossovers are cultured in LB-G broth supplemented with 10% sucrose at 37° C. with gentle agitation for 16 hours. Serial dilutions of the overnight cultures are plated onto LB-G plates supplemented with 10% sucrose and incubated at 37° C. for 16 hours.

i) Colonies which grow on the 10% sucrose LB-G plates are subcultured onto each of LB-G, LB-G + gentamicin and streptomycin and minimal and incubated at 37° C. for 16 hours. Colonies only growing on the LB-G plates (double crossovers) are subcultured onto 5% sheep's blood agar and maintained at 4° C.

IV) Intermediate Cloning Vector

Suicide vector (SacB, PNG101) was the intermediate cloning vector. Conjugation was performed between donor (S17 harboring PNG101 with aroA harboring 100 bp deletion) and wild-type *E. coli* isolate.

EXAMPLE 2
Preparation of Master Seed

The *E. coli* aroA-strain (constructed in Example 1) is grown on tryptic soy agar plate once and passed 3 times in tryptic soy broth. The culture is distributed into glass vials, sealed and lyophilized.

EXAMPLE 3

Evaluation of the Efficacy of *E. coli* aroA-Live Vaccine in Chickens Against Avian Colibacillosis After One Vaccination In this evaluation, 96 SPF white leghorn chickens are divided into 3 groups of 32 each. Birds are hand picked and placed in an arbitrarily assigned isolater. Each test group is housed in 2 isolaters containing 16 birds each.

Group A is vaccinated at 1 day old by coarse spray using a hand-held sprayer. At one day of age, birds in test group A are grouped together in a small container and the vaccine is sprayed to the heads of the birds until the calibrated dosage has been given. The *E. coli* aroA-microorganism of Example 2 is diluted with sterile phosphate buffered saline (PBS) to a titer of $5.0 \times 10^6$ cfu per dose (1 mL per bird).

At 6 weeks of age, Group A and Group B (unvaccinated) are challenged intratracheally (IT) with a 1.0 mL dose of $1.0 \times 10^9$ cfu *E. coli* O78.

Test Group C is unvaccinated and unchallenged (negative control group). Vaccinates and control birds are reared in separate isolaters until the completion of the study.

All birds are under veterinary care with feed and water available ad libitum. Birds are observed daily for 7 days post-challenge. At the end of the 7-day post-challenge period, all surviving birds are necropsied and examined for the presence of lesions typical of colibacillosis. Non-surviving birds and birds that demonstrated any of the grossly visible lesions such as perihepatitis, pericarditis, airsacculitis, cellulitis, or arthritis are considered positive for colibacillosis.

The results are shown in Table I.

TABLE I

| Test Group | Vaccination Route | Challenge Route | % Mortality | % Surviving birds with gross lesions | | | | | % Positive for Colibacillosis |
|---|---|---|---|---|---|---|---|---|---|
| | | | | Hep[b] | Card[c] | Air[d] | Cell[e] | Arth[f] | |
| A | Coarse spray | IT | 3.1[a] | 22.6 | 6.5 | 16.13 | 3.2 | 0 | 29.0 |
| B | None | IT | 28.1 | 91.3 | 82.6 | 86.9 | 47.8 | 17.4 | 96.9 |
| C | None | None | 0 | 0 | 0 | 0 | 0 | 0 | 0 |

[a]One bird died at one day post-vaccination. The cause could not be determined but was likely non-specific early chick mortality often related to yolk sac or navel infection.
[b]Perihepatitis
[c]Pericarditis
[d]Airsacculitis
[e]Cellulitis
[f]Arthritis As can be seen from the data in Table I, the *E. coli* aroA-vaccine of the invention is safe and efficacious for the prevention of colibacillosis in chickens caused by *E. coli* O78, when said vaccine is administered at one day of age.

EXAMPLE 4

Evaluation of the Efficacy of *E. coli* aroA-Live Vaccine in Chickens Against Avian Colibacillosis After Two Vaccinations In this evaluation, 96 SPF white leghorn chickens are divided into 3 groups of 32 each. Birds are hand picked and placed in an arbitrarily assigned isolater. Each test group is housed in 2 isolaters, each containing 16 birds.

Group A (vaccinates) are vaccinated at one day of age by coarse spray, as described in Example B and again at 1 week of age by the drinking water route. At one week of age, birds are deprived of drinking water for 3 h. The *E. coli* aroA-vaccine of Example 2 is diluted and mixed with a measured quantity of cool distilled water to a final titer of $5.0 \times 10^6$ cfu. The measured quantity of distilled water is that amount previously determined to be consumed in one hour.

At 6 weeks of age, Group A (vaccinated) and Group B (unvaccinated) are challenged intratracheally (IT) with a 1.0 mL dose of $1.0 \times 10^9$ cfu *E. coli* O78.

Test Group C is unvaccinated and unchallenged (negative control group). Vaccinates and control birds are reared in separate isolaters until the completion of the study.

All birds are under veterinary care with feed and water available ad libitum. Birds are observed daily for 7 days post-challenge. At the end of the 7-day post-challenge period, all surviving birds are necropsied and examined for the presence of lesions typical of colibacillosis. Non-surviving birds and birds that demonstrated any of the grossly visible lesions such as perihepatitis, pericarditis, airsacculitis, cellulitis, or arthritis are considered positive for colibacillosis.

The results are shown in Table II.

7 days post challenge, all surviving birds were necropsied and examined for the presence of grossly visible lesions typical of colibacillosis (perihepatitis, pericarditis, airsacculitis, cellulitis, or arthritis).

There were no unfavorable reactions (death or other clinical signs) that were attributable to the administration of FDAH *E. coli* aroA-live vaccine, an indication of its safety for mass administration.

The virulent strain of *E. coli* O78 caused 28.1% mortality (9 out of 32 birds died) in the unvaccinated challenged controls (group #2) during the 7-day post-challenge period. The mortality caused by virulent strain of *E. coli* O78 in FDAH *E. coli* aroA-live vaccine vaccinated birds was 0% (0 out of 32 birds died) during the 7-day post-challenge period.

The rates of colibacillosis were statistically analyzed between vaccinated challenged birds and unvaccinated challenged control birds. There was a significant difference (p<0.0001) between the vaccinated and unvaccinated challenged birds with gross lesions typical of colibacillosis. The prevented fraction was 72.4% (95% CI 53.7, 83.6).

Based on the present study, it was concluded that FDAH *E. coli* aroA-live vaccine with a titer of $3.2 \times 10^6$ cfu per dose was safe and efficacious for the prevention of colibacillosis in chickens caused by *E. coli* O78 when it was administered at one day of age by coarse spray and again at 1 week of age in the drinking water.

TABLE II

| Test Group | Vaccination Route | Challenge Route | % Mortality | % Surviving birds with gross lesions | | | | | % Positive for Colibacillosis |
|---|---|---|---|---|---|---|---|---|---|
| | | | | Hep[b] | Card[c] | Air[d] | Cell[e] | Arth[f] | |
| A | Coarse Spray/Drinking Water | IT | 6.3[a] | 10 | 23.3 | 20 | 0 | 0 | 36.7 |
| B | None | IT | 28.1 | 91.3 | 82.6 | 86.9 | 47.8 | 17.4 | 96.9 |
| C | None | None | 0 | 0 | 0 | 0 | 0 | 0 | 0 |

[a]Two birds died at 2 days post-vaccination via the coarse spray route. The cause could not be determined but was likely nonspecific early chick mortality often related to yolk sac or navel infection.
[b]Perihepatitis
[c]Pericarditis
[d]Airsacculitis
[e]Cellulitis
[f]Arthritis As can be seen from the data in Table II, the *E. coli* aroA-vaccine of the invention is safe and efficacious for the prevention of colibacillosis in chickens caused by *E. coli* O78, when said vaccine is administered at one day of age via coarse spray and again at one week of age via drinking water.

EXAMPLE 5

Further Evaluation of the Efficacy of *E. coli* aroA-Live Vaccine in Chickens Against Avian Colibacillosis (Serotype O78) After Two Vaccinations This study investigated the efficacy of an *E. coli* aroA-live vaccine in preventing colibacillosis in chickens following intratracheal challenge with a virulent strain of *E. coli*-serotype O78. Each bird in test group #1 (32 birds) was vaccinated by coarse spray at 1 day of age and again in the drinking water at 1 week of age with one bird dose of *E. coli* aroA-vaccine. Birds in test group #2 (32 birds) served as unvaccinated challenged controls. Birds in test group #3 (32 birds) were not vaccinated and were not challenged. All the birds in groups #1 and #2 were challenged intratracheally at 6 weeks of age with $1.5 \times 10^9$ cfu per dose of *E. coli* O78. At

EXAMPLE 6

Further Evaluation of the Efficacy of *E. coli* aroA-Live Vaccine in Chickens Against Avian colibacillosis (Serotype O78) After One Vaccination This study investigated the efficacy of an *E. coli* aroA-live vaccine in preventing colibacillosis in chickens following intratracheal challenge with a virulent strain of *E. coli* O78. Each bird in test group #1 (32 birds) was vaccinated by coarse spray at 1 day of age with one bird dose of *E. coli* aroA-vaccine. Birds in test group #2 (32 birds) served as unvaccinated challenged controls. Birds in test group #3 (32 birds) were not vaccinated and were not challenged. All the birds in groups #1 and #2 were challenged intratracheally at 6 weeks of age with $1.5 \times 10^9$ cfu per dose of *E. coli* O78. At 7 days post challenge, all surviving birds were necropsied and examined for the presence of grossly visible lesions typical of colibacillosis (perihepatitis, pericarditis, airsacculitis, cellulitis, or arthritis).

There were no unfavorable reactions (death or other clinical signs) that were attributable to the administration of FDAH *E. coli* aroA-live vaccine, an indication of its safety for mass administration.

The virulent strain of *E. coli* O78 caused 28.1% mortality (9 out of 32 birds died) in the unvaccinated challenged controls during the 7-day post-challenge period. The mortality caused by virulent strain of *E. coli* O78 in FDAH *E. coli* aroA-live vaccine vaccinated birds was 0% (0 out of 32 birds died) during the 7-day post-challenge period.

The rates of colibacillosis were statistically analyzed between vaccinated challenged birds and unvaccinated challenged control birds. There was a significant difference (p<0.0001) between the vaccinated and unvaccinated challenged birds with gross lesions typical of colibacillosis. The prevented fraction was 76.5% (95% Cl 57.9, 86.9).

Based on the present study, it was concluded that FDAH *E. coli* aroA-live vaccine containing $3.2 \times 10^6$ cfu per dose was safe and efficacious for the prevention of colibacillosis in chickens caused by *E. coli* O78 when it was administered at one day of age by coarse spray.

EXAMPLE 7

Evaluation of the Efficacy of *E. coli* aroA-Live Vaccine in Chickens Against Avian Colibacillosis (Virulent Untyped Serotype) After Two Vaccinations This study investigated the efficacy of an *E. coli* aroA-live vaccine in preventing colibacillosis in chickens following intratracheal challenge with a virulent *E. coli* which is untyped. Each bird in test group #1 (32 birds) was vaccinated by coarse spray at 1 day of age and again in the drinking water at 1 week of age with one bird dose of *E. coli* aroA-vaccine. Birds in test group #2 (32 birds) served as unvaccinated challenged controls. Birds in test group #3 (32 birds) were not vaccinated and were not challenged. All the birds in groups #1 and #2 were challenged intratracheally at 6 weeks of age with $2.5 \times 10^{10}$ cfu per dose of virulent *E. coli*. At 7 days post challenge, all surviving birds were necropsied and examined for the presence of grossly visible lesions typical of colibacillosis (perihepatitis, pericarditis, airsacculitis, cellulitis, or arthritis).

There were no unfavorable reactions (death or other clinical signs) that were attributable to the administration of FDAH *E. coli* aroA-live vaccine, an indication of its safety for mass administration.

The virulent *E. coli* did not cause mortality in the unvaccinated challenged controls or the FDAH *E. coli* aroA-live vaccine vaccinated birds during the 7-day post-challenge period.

The rates of colibacillosis were statistically analyzed between vaccinated challenged birds and unvaccinated challenged control birds. There was a significant difference (p<0.0001) between the vaccinated and unvaccinated challenged birds with gross lesions typical of colibacillosis. The prevented fraction was 87.1% (95% Cl 61.9, 95.6).

Based on the present study, it was concluded that FDAH *E. coli* aroA-live vaccine with a titer of $3.2 \times 10^6$ cfu per dose was safe and efficacious for the prevention of colibacillosis in chickens caused by virulent *E. coli* when it was administered at one day of age by coarse spray and again at 1 week of age in the drinking water.

EXAMPLE 8

Evaluation of the efficacy of *E. coli* aroA-Live Vaccine in Chickens Against Avian Colibacillosis (Virulent Untyped Serotype) After One Vaccination This study investigated the efficacy of an *E. coli* aroA-live vaccine in preventing colibacillosis in chickens following intratracheal challenge with a virulent *E. coli* which is untyped. Each bird in test group #1 (32 birds) was vaccinated by coarse spray at 1 day of age with one bird dose of *E. coli* aroA-vaccine. Birds in test group #2 (32 birds) served as unvaccinated challenged controls. Birds in test group #3 were unvaccinated and were not challenged. All the birds in groups #1 and #2 were challenged intratracheally at 6 weeks of age with $2.5 \times 10^{10}$ cfu per dose of virulent *E. coli*. At 7 days post challenge, all surviving birds were necropsied and examined for the presence of grossly visible lesions typical of colibacillosis (perihepatitis, pericarditis, airsacculitis, cellulitis, or arthritis).

There were no unfavorable reactions (death or other clinical signs) that were attributable to the administration of FDAH *E. coli* aroA-live vaccine, an indication of its safety for mass administration.

The virulent *E. coli* did not cause mortality in the unvaccinated challenged controls or the FDAH *E. coli* aroA-live vaccine vaccinated birds during the 7-day post-challenge period.

The rates of colibacillosis were statistically analyzed between vaccinated challenged birds and unvaccinated challenged control birds. There was a significant difference (p<0.0001) between the vaccinated and unvaccinated challenged birds with gross lesions typical of colibacillosis. The prevented fraction was 66.6% (95% Cl 39.8, 81.5).

Based on the present study, it was concluded that FDAH *E. coli* aroA-live vaccine with a titer of $3.2 \times 10^6$ cfu per dose was safe and efficacious for the prevention of colibacillosis in chickens caused by virulent *E. coli* when it was administered at one day of age by coarse spray.

EXAMPLE 9

Comparative Study A

In this study, the vaccine of the invention was compared against the commercial GARAVAX®-T vaccine, a competitor's product, which is a live bacterial vaccine containing an avirulent temperature sensitive mutant of *E. coli*, and is recommended for use in turkeys to aid in the prevention of colibacillosis associated with infection by *E. coli* serotype O78.

Each bird in test group #1 (30 birds) was vaccinated by coarse spray at 1 day of age and again in the drinking water at 2 weeks of age with one bird dose of *E. coli* aroA-vaccine according to one embodiment of the invention (passage level X+5; $5.0 \times 10^6$ cfu per 1 mL dose). Birds in test group #2 (30 birds) were each vaccinated by coarse spray at 1 day of age and again in the drinking water at 2 weeks of age with one bird dose of GARAVAX®-T vaccine, following recommended label directions. Birds in test group #3 (30 birds) served as unvaccinated challenged controls. Birds in test group #4 (30 birds) were not vaccinated and were not challenged. All the birds in groups #1, #2 and #3 were challenged intratracheally at 6 weeks of age with a target dose of $5 \times 10^9$ cfu per dose (1.0 mL/dose) of a virulent *E. coli* O78. At 7 days post challenge, the number of dead birds was noted and all surviving birds were necropsied and examined for the presence of grossly visible lesions typical of colibacillosis.

The results are set forth in Table III below—the percentages of chickens with specific airsacculitis and overall colibacillosis lesions is quantified therein:

TABLE III

| Group No. | Vaccination Route | Challenge Route | Total No. Birds | Airsacculitis | Colibacillosis | % Positive for Airsacculitis[1] | % Positive for Colibacillosis[2] |
|---|---|---|---|---|---|---|---|
| EFFICACY OF LIVE *E. COLI* AROA-VACCINE IN PREVENTING AIRSACCULITIS IN CHICKENS AGAINST *E. COLI* O78 CHALLENGE | | | | | | | |
| 1 | CS/DW | Intratracheally | 30 | 2 | 2 | 6.6 (2/30[a]) | 6.6 (2/30[a]) |
| 3 | None | Intratracheally | 30 | 16 | 19 | 53.3 (16/30[b]) | 63.3 (19/30[b]) |
| EFFICACY OF GARAVAX ®-T VACCINE IN PREVENTING AIRSACCULITIS IN CHICKENS AGAINST *E. COLI* O78 CHALLENGE | | | | | | | |
| 2 | CS/DW | Intratracheally | 30 | 8 | 10 | 26.7 (8/30[a]) | 33.3 (10/30[a]) |
| 3 | None | Intratracheally | 30 | 16 | 19 | 53.3 (16/30[b]) | 63.3 (19/30[b]) |

[1]% Positive for airsacculitis = Total # of birds with airsacculitis/total # of birds
[2]% Positive for colibacillosis = Total # of birds with colibacillosis lesions and birds dead/total # of birds
CS = Coarse Spray
DW = Drinking Water
Values within the same column followed by different letters are significantly different (Chi-square test: $p < 0.05$)

EXAMPLE 10

Comparative Study B

In this study, the vaccine of the invention was compared against the commercial GARAVAX®-T vaccine, a competitor's product, which is a live bacterial vaccine containing an avirulent temperature sensitive mutant of *E. coli*, and is recommended for use in turkeys to aid in the prevention of colibacillosis associated with infection by *E. coli* serotype O78.

Each bird in test group #1 (31 birds) was vaccinated by coarse spray at 1 day of age and again in the drinking water at 2 weeks of age with one bird dose of *E. coli* aroA-vaccine according to one embodiment of the invention (passage level X+5; $5.0 \times 10^6$ cfu per 1 mL dose). Birds in test group #2 (29 birds) were each vaccinated by coarse spray at 1 day of age and again in the drinking water at 2 weeks of age with one bird dose of GARAVAX®-T vaccine, following recommended label directions. Birds in test group #3 (31 birds) served as unvaccinated challenged controls. Birds in test group #4 (30 birds) were not vaccinated and were not challenged; none of these died. All the birds in groups #1, #2 and #3 were challenged intratracheally at 6 weeks of age with a target dose of $5.0 \times 10^9$ cfu per dose (1.0 mL/dose) of a virulent *E. coli* 624 (untyped serotype). At 7 days post challenge, the number of dead birds was noted and all surviving birds were necropsied and examined for the presence of grossly visible lesions typical of colibacillosis.

The results are set forth in Table IV below—the percentages of chickens with specific cellulitis is quantified therein:

TABLE IV

| Group No. | Vaccination Route | Challenge Route | Total No. Birds | Cellulitis | No. Dead Birds | % Positive for Cellulitis[1] |
|---|---|---|---|---|---|---|
| EFFICACY OF LIVE *E. COLI* AROA-VACCINE IN PREVENTING CELLULITIS IN CHICKENS AGAINST *E. COLI* 624 (UNTYPED SEROTYPE) CHALLENGE | | | | | | |
| 1 | CS/DW | Intratracheally | 31 | 6 | 8 | 45.2 (14/31[a]) |
| 3 | None | Intratracheally | 31 | 4 | 20 | 77.4 (24/31[b]) |
| EFFICACY OF GARAVAX ®-T VACCINE IN PREVENTING CELLULITIS IN CHICKENS AGAINST *E. COLI* 624 (UNTYPED SEROTYPE) CHALLENGE | | | | | | |
| 2 | CS/DW | Intratracheally | 29 | 7 | 12 | 65.5 (19/29[a]) |
| 3 | None | Intratracheally | 31 | 4 | 20 | 77.4 (24/31[a]) |

[1]% Positive for Cellulitis = Total # of birds w/cellulitis and birds dead/total # of birds CS = Coarse Spray DW = Drinking Water Values within the same column followed by different letters are significantly different (Chi-square test: $p < 0.05$)

What is claimed is:

1. A vaccine composition which comprises an immunogenically effective amount of an isolated mutant *E. coil* strain and a pharmacologically acceptable carrier, wherein the mutant *E. coli* strain is the strain deposited at the American Type Culture Collection under assigned number PTA-5094.

2. The composition according to claim 1 wherein said carrier is a balanced salt solution suitable for use in tissue or cell culture media.

3. The composition according to claim 1 wherein said carrier is distilled water.

4. The composition according to claim 1 wherein the immunogenically effective amount is an amount sufficient to provide about $5.0 \times 10^2$ cfu to $5.0 \times 10^{10}$ cfu.

5. The composition according to claim 4 wherein said effective amount is about $5.0 \times 10^6$ cfu to $6.0 \times 10^6$ cfu.

6. A method for the prevention or amelioration of colibacillosis in poultry which comprises administering to said poultry an immunogenically effective amount of a mutant *E. coil* strain, wherein the mutant *E. coil* strain is the strain deposited at the American Type Culture Collection under assigned number PTA-5094.

7. The method according to claim 6 wherein the poultry is selected from the group consisting of: chickens; ducks; geese; turkeys; bantams; quail; pheasant; and pigeons.

8. The method according to claim 6 wherein said mutant *E. coli* strain is administered via mass application.

9. The method according to claim 6 wherein said immunogenically effective amount is about $5.0 \times 10^2$ cfu to $5.0 \times 10^{10}$ cfu.

10. The method according to claim 7 wherein said poultry are chickens or turkeys.

11. The method according to claim 8 wherein said mutant *E. coli* strain is administered by spray application.

12. The method according to claim 8 wherein said mutant *E. coli* strain is administered in the drinking water.

13. The method according to claim 10 wherein said poultry are chickens.

14. The method according to claim 13 wherein said immunogenically effective amount is about $5.0 \times 10^6$ cfu to $6.0 \times 10^6$ cfu.

15. A method for the prevention or amelioration of cellulitis in poultry which comprises administering to said poultry an immunogenically effective amount of a mutant *E. coil* strain, wherein the mutant *E. coil* strain is the strain deposited at the American Type Culture Collection under assigned number PTA-5094.

16. A vaccine composition which comprises an immunogenically effective amount of a mutant *E. coli* strain and a pharmacologically acceptable carrier, wherein the mutant *E. coli* strain is the strain deposited at the American Type Culture Collection under assigned number PTA-5094, wherein said vaccine is safe and effective for mass application via aerosol spray or drinking water, and said immunogenically effective amount is sufficient to provide about $3.0 \times 10^6$ cfu to $6.0 \times 10^6$ cfu.

17. An *Escherichia coil* microorganism strain deposited at the American Type Culture Collection under assigned number PTA-5094.

* * * * *

UNITED STATES PATENT AND TRADEMARK OFFICE
CERTIFICATE OF CORRECTION

PATENT NO. : 7,357,935 B2  Page 1 of 1
APPLICATION NO. : 10/837793
DATED : April 15, 2008
INVENTOR(S) : Henry H. Fan et al.

It is certified that error appears in the above-identified patent and that said Letters Patent is hereby corrected as shown below:

Column 13  Line 3, replace "coil" with "coli"
          Line 21, replace "coil strain, wherein the mutant E. coil" with "coli strain, wherein the mutant E. coli"

Column 14  Line 4, replace "coil" with "coli"
          Line 6, replace "coil" with "coli"
          Line 15, replace "coil strain, wherein the mutant E. coil" with "coli strain, wherein the mutant E. coli"
          Line 27, replace "coil" with "coli"

Signed and Sealed this

Ninth Day of June, 2009

JOHN DOLL
*Acting Director of the United States Patent and Trademark Office*